United States Patent [19]

Hagiwara

[11] Patent Number: 5,139,741
[45] Date of Patent: Aug. 18, 1992

[54] BLOOD PROCESSING APPARATUS OF HOLLOW FIBER TYPE

[75] Inventor: Kazuhiko Hagiwara, Fuji, Japan

[73] Assignee: Terumo Kabushi Kaisha, Tokyo, Japan

[21] Appl. No.: 457,263

[22] Filed: Dec. 27, 1989

[30] Foreign Application Priority Data

Dec. 29, 1988 [JP] Japan .................................. 63-335068
Jan. 6, 1989 [JP] Japan ..................................... 64-896

[51] Int. Cl.$^5$ .............................................. A61M 1/03
[52] U.S. Cl. .................................. 422/48; 210/321.81;
  210/321.9; 210/416.1; 128/DIG. 3; 261/DIG. 28
[58] Field of Search ............ 422/45, 48; 128/DIG. 3;
  261/DIG. 28; 210/321.81, 321.9, 416.1

[56] References Cited

U.S. PATENT DOCUMENTS

| 4,374,802 | 2/1983 | Fukasawa | 422/48 |
| 4,424,190 | 1/1984 | Mather et al. | 422/46 |

FOREIGN PATENT DOCUMENTS 60-5308 2/1985 Japan .
62-211072 9/1987 Japan .
62-54510 11/1987 Japan .

Primary Examiner—Lynn M. Kummert
Attorney, Agent, or Firm—Frishauf, Holtz, Goodman & Woodward

[57] ABSTRACT

A housing accommodates a hollow fiber bundle such that a blood port zone is defined between an open end surface of the hollow fiber bundle and an inner wall surface of the housing. The blood port zone includes an increased distance space, which is formed annularly along an edge portion of the open end surface of the hollow fiber bundle and communicates with the blood port, and a small distance space, which communicates with the blood port and has an end wall surface substantially parallel to V, and at a small distance from V, the open end surface of the hollow fiber bundle. A movable member, such as a flexible membrane facing the end surface of the hollow fiber bundle, is provided for varying the volume of the blood port zone. A restriction is provided for restricting the movement of the movable member. Due to a difference in resistance offered to blood between the increased and small distance spaces, blood flows uniformly over the entire end surface of the hollow fiber bundle, thus positively preventing stagnation of blood in the blood port zone.

11 Claims, 10 Drawing Sheets

BLOOD PROCESSING APPARATUS OF HOLLOW FIBER TYPE

BACKGROUND OF THE INVENTION

This invention relates to a blood processing apparatus of hollow fiber type with a plurality of hollow fibers used for extracorporeal circulation of blood to effect dialysis, purification, gas exchange, etc. of blood.

This kind of hollow fiber type blood processing apparatus is extensively used as oxygenators and dialyzers. As an example, an oxygenator apparatus as shown in FIG. 1 is well known as an aid (ECMO: Extracorporeal Membrane Oxygenation) to an organic lung by extracorporeal circulation. This structure will now be described briefly.

Reference numeral 1 designates a hollow fiber bundle having a plurality of hollow fibers, through which blood flows. This hollow fiber bundle 1 has its opposite ends embeddedly secured to and supported by respective partitioning walls 2 which isolate, in a liquid tight manner, a blood processing chamber 3a and blood port zones 4a to be described later from one another such that the hollow fibers are open to the zones 4a. The periphery of hollow fiber bundle 1 is covered by a housing 3, while the opposite ends of the bundle 1 are covered by liquid port covers 4 which constitute part of housing 3. Housing 3 includes a cylindrical body 5 and mount covers 6 fittedly mounted on the opposite ends of the cylindrical body 5. The mount covers 6 are held in close contact with the periphery of partitioning walls 2, thus forming a blood processing chamber 3a in housing 3. Mount covers 6 are provided with gas ports 3b for supplying oxygen for gas exchange with blood. A flow path is formed in chamber 3a.

Each port cover 4 defines an inner conical blood port zone 4a flaring toward end face 1a of hollow fiber bundle 1, and it has a blood port 4b provided at its free end and extending along axis X—X of the hollow fiber bundle and a flange 7 provided at its flaring end. Blood port cover nut 8 having annular flange 8a is screwed on mount cover 6 of housing 3 such that annular flange 8a urges the outer surface of flange 7. Flange 7 is held in close contact via packing 9 with an edge portion of partitioning wall 2.

The oxygenator of this structure is of internal return flow type, and in which blood enters the hollow fibers from one blood port 4b and through one blood port zone 4a, and as it passes through the hollow fibers carbon dioxide gas in it is exchanged through the hollow fibers with oxygen supplied to blood processing chamber 3a from one gas port 3b. Blood gaining oxygen is returned to the organism through the other blood port zone 4a and the other blood port 4b. Carbon dioxide gas removed from blood is let to the outside from the other gas port 3b.

In the above prior art oxygenator, the area of end surface 1a of hollow fiber bundle 1 is considerably large compared to the area of blood port 4b. Therefore, the speed of blood flowing through blood port zone 4a is not uniform. More specifically, the speed of blood flowing into or out of the hollow fibers is high in a central portion of end surface 1a right underneath or right above blood port 4b because the flow is led directly to or from port 4b, while it is low in edge portion of end surface 1a because the distance to the port is increased. Therefore, in blood port zone 4a at the edge of hollow fiber bundle the flow of blood is very low so that a stagnant state results or, in some cases, is completely stopped. In such a case, precipitation of blood cells is produced in a peripheral portion of hollow fiber bundle 1. If this occurs, it undesirably leads to formation of thrombus and further clogging of hollow fiber bundle 1.

Further, in the oxygenator of vertical type as shown in FIG. 1, blood is caused to flow either downwardly from the upper blood port zone to the lower one or in the converse direction, i.e., upwardly. The stagnation of blood in blood port zone 4a is produced pronouncedly in blood port zone 4a on the inlet side in the case of the downward flow and one on the outlet side in the case of the upward flow due to the influence of the gravitational force. A solution to this problem is particularly desired.

To solve this problem, there have heretofore been proposed a structure, in which the peripheral wall of the liquid port zone has a curved surface based on a predetermined calculation, and a structure, which has a particular blood port zone shape such as a revolving flow type. Examples of such structures are disclosed in Japanese Patent Publications No.62-54510 and No.60-5308 and Japanese Patent Disclosure No.62-21107.

However, stagnation of blood can not be sufficiently prevented even with these proposed blood processing apparatuses. More specifically, where downward blood flow is caused, stagnation of blood in a peripheral portion of hollow fiber bundle still can not be prevented with the apparatus, in which the peripheral surface of the inlet side blood port zone has a curved shape based on a predetermined calculation, while with the apparatus of the revolving flow type it is produced in a central portion of the hollow fiber bundle although it is prevented in the peripheral portion.

Further, the proposed structures mainly aim at prevention of blood stagnation in the inlet side blood port zone which is particularly significant where downward blood flow is caused. That is, they neither aim nor provides for any expected effect of prevention of blood stagnation in the outlet side blood port zone which is particularly significant where upward blood flow is caused.

Particularly, with recent development of materials having compatibility to blood, non-heparin extracorporeal circulation without use of heparin or like agent against coagulation of blood is being tried. In this case, the stagnation of blood causes clogging of the hollow fiber bundle and formation of thrombus, and it is fatal if extracorporeal circulation is performed for a long time, thus posing significant quality and safety problems.

Further, in extracorporeal circulation using an oxygenator, it is usual in view of the arrangement of the blood circuit and priming operation and also in case of coupling a heat exchanger to the oxygenator, to dispose the apparatus vertically for causing upward blood flow from the considerations of the safety of a heavy and large heat exchanger filled with water. In such cases, therefore, the stagnation of blood in the outlet side blood port zone presents particular significant problems.

Further, where a centrifugal pump or like constant flow pump is used for upward blood flows, blood flow not pulsatingly but constantly, and therefore in the blood port zone blood stagnation is liable to be produced in the peripheral portion.

Further, this kind of blood processing apparatus has the following problems.

As blood processing apparatus where extracorporeal circulation is performed there are oxygenators and dialyzers, and for enhancing the effect of processing recirculating blood led out from the organism back to the blood processing apparatus is in considerable practice in therapeutical processes, in which $CO_2$ in blood is removed by extracorporeal circulation. The recirculation is usually performed with a system as shown in FIG. 2(a), in which two reservoirs R1 and R2 and two pumps P1 and P2 are provided, or with a system as shown in FIG. 2(b), in which only two pumps P1 and P2 are provided, i.e., no reservoir is provided, in the recirculation circuit.

With the system with the reservoirs, however, a great amount of blood is circulated. Extracorporeal circulation without use of any anti-coagulation agent is also tried to prevent bleeding when the apparatus is used continuously for a long time. In this case, however, the system with the storage units can not be utilized because thrombus is formed in the stagnated part of the blood.

Further, even with the system without use of any storage unit, extreme pressure variations are liable depending on the timing of operation of the two pumps, and an increase of the amount of recirculation may produce a negative pressure in the outlet side blood port zone in the blood processing apparatus. This not only leads to rupture of blood cells, but if the hollow fiber film is porous, the possibility of introduction of air bubbles is increased, thus making it difficult to continue operation. Further, in the inlet side blood port zone an increase of the amount of recirculation may produce positive pressure, thus leading to the rupture of blood cells.

In order to prevent this, it is tried to hold the pumps in a non-occulusive state. In this case, however, reverse flow or idling is liable to be produced, making it difficult to grasp the amount of blood and also causing extreme damage to blood. Besides, doing so is hardly ineffective in the prevention of negative pressure generation.

SUMMARY OF THE INVENTION

The present invention has been intended in the light of the problems discussed above, and it has an object of providing a blood processing apparatus, which can cause satisfactory flow of blood over the entire blood port zone irrespective of whether the blood flow is upwards or downwards, thus positively preventing the stagnation, and also permits uniform flow of blood into or out the hollow fiber bundle at any position thereof, thus preventing the clogging of the hollow fiber bundle and thrombus and improving the quality and safety.

Another object of the invention is to provide a blood processing apparatus, which, although with use of pumps in a perfectly occulusive state, for instance, roller pumps, can prevent generation of undesired pressure in the circuit, particularly generation of negative pressure or momentary abnormal pressure variations, thus permitting ready and safe blood processing by extracorporeal circulation.

To attain the above objects of the invention, there is provided a blood processing apparatus of hollow fiber type, which comprises a hollow fiber bundle having a large number of hollow fibers, through which blood flows, and having open end surfaces constituted by the open ends of said hollow fibers, a housing accommodating said hollow fiber bundle, a blood port zone defined between said housing and each end surface of said hollow fiber bundle, and a blood port provided on said housing and open to said blood port zone, said blood port zone including an increased distance space communicating with said blood port, having an annular shape extending along the edge of said end surface of said hollow fiber bundle and extending away from said end surface, and a small distance space communicating with said increased distance space and having an end wall surface extending substantially parallel to and at a small distance from said end surface of said hollow fiber bundle.

With the blood processing apparatus having the above construction according to the invention, the flow of blood in the blood port zone is reduced with increase of the resistance offered to the blood and increased with reduction of the resistance. Thus, the resistance against flow is high in the small distance space and low in the increased distance space, that is, blood flows at a higher rate in the increased distance space. Thus, with the increased distance space provided along an edge portion of the end surface of the hollow fiber bundle, sufficient blood flow can be ensured in an edge portion of the blood port zone as well, in which stagnation is liable to be produced. Thus, blood flow can be caused uniformly over the entire end surface of the hollow fiber bundle in either central or edge portion thereof. It is thus posible to prevent stagnation of blood in the blood port zone positively.

As a preferred structure of the blood processing apparatus according to the invention, the small distance space is defined annularly by a rib projecting integrally from the inner wall surface of the housing and radially inwardly adjacent to the increased distance space toward the end surface of the hollow fiber bundle, and the blood port zone includes a central increased distance space communicating with the small distance space, formed radially inwardly of the small distance space and having a wall surface at an increased distance from the end surface of the hollow fiber bundle compared to the end wall surface defining the small distance space. The rib has a notch formed on the side of the axis of the hollow fiber bundle diametrically opposite the blood port, and the central increased distance space communicates with the annular increased distance space via the notch.

With this structure with the annular small distance space, which offers high resistance against blood flow, uniform blood flow can be obtained. Further with the notch formed in the annular rib defining the small distance space at a position opposite the blood port, sufficient blood flow can be secured in a portion where stagnation is most liable to be produced.

As a further preferred structure according to the invention, the distance between the inner wall surface defining the small distance space and the end surface of the hollow fiber bundle is 1/20 to 1/300 of the diameter of the hollow fiber bundle. With this arrangement, more uniform flow of blood can be obtained in the blood port zone to reliably prevent blood stagnation. In addition, there is no possibility of rupture of blood cells despite increase of the resistance offered to blood in the small distance space.

As a further preferred structure according to the invention, the length of the notch is preferably no greater than 2/5 of the length of a circle passing the center of the rib.

In a further preferred structure of the blood processing apparatus of hollow fiber type according to the invention, movable wall means is provided, which can vary the volume of the blood port zone. The movable wall means is comprises by a movable member facing the end surface of the hollow fiber bundle via the blood port zone and supported by the housing such that it is substantially parallel to the end surface of the hollow fiber bundle and movable in the axial direction thereof toward and away from the end surface of the hollow fiber bundle. The movable member, which is circular in shape correspond to the circular end surface of the hollow fiber bundle, has a central increased distance space projecting into the blood port zone toward the end surface of the hollow fiber bundle.

With this structure, provided with the movable member, it is possible to produce an adequate and positive turbulent flow of blood in the blood port zone, thus precluding stagnation in the blood port zone and obtaining satisfactory blood flow therein.

In a further preferred structure according to the invention, the movable wall means comprises an elastically deformable flexible membrane provided in the housing.

The flexible membrane can be deformed by externally applying pressure to it, and by so doing the same function as with the movable member noted above can be obtained. In addition, with the flexible membrane it is possible to absorb abnormal pressure variations such as negative or positive pressure generated in a blood circulation circuit during operation of two pumps in the circuit.

In a further preferred structure according to the invention, restricting means for restricting the deformation of the flexible membrane is provided. The restricting means comprises by a net-like member, which is formed spherically on the inner wall surface of the housing or stretched in the housing. With this restricting means it is possible to prevent excessive deformation of the flexible membrane and to provide a safer and more durable apparatus.

DETAILED DESCRIPTION OF THE PREFERRED EMBODIMENTS

Now, preferred embodiments of the blood processing apparatus of hollow fiber type according to the invention will be described in conjunction with oxygenators and with reference to FIGS. 3 to 19.

Figure 4:
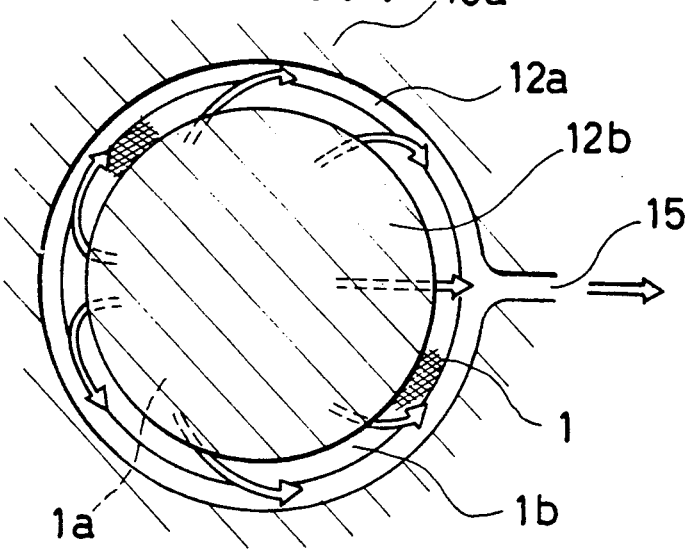
FIGS. 4 and 5 are fragmentary sectional views taken along line A—A in FIG. 3 for explaining the status of blood flow.
Figure 5:
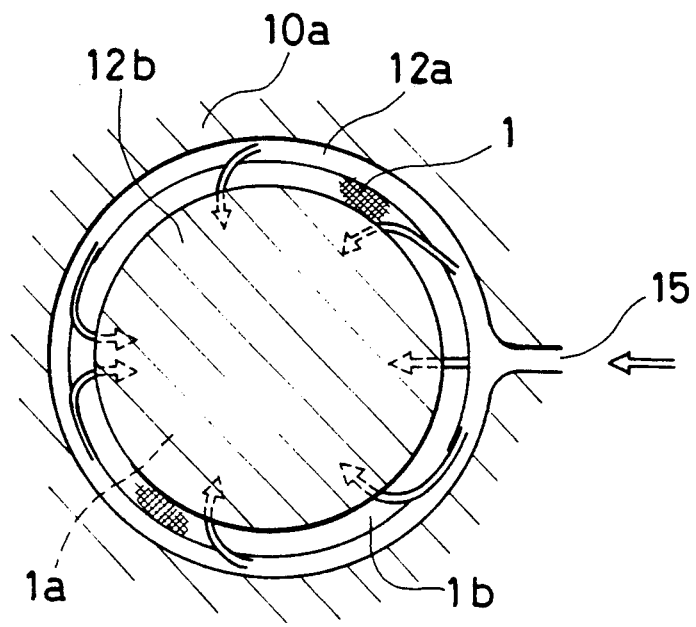

First, an oxygenator as a first embodiment of the invention will be described with reference to FIGS. 3 to 5. Referring to the Figures, reference numeral 1 designates a hollow fiber bundle comprising a plurality of hollow fibers, 2 a partitioning wall, 3 a housing defining blood processing chamber 3a and having medium port 3b for supplying oxygen as a medium for gas exchange of blood, 5 a cylindrical body of housing 3 having rib 5a and constriction 5b, and 6 a mount cover. The above parts are like those described before in connection with the prior art apparatus shown in FIG. 1.

Reference numeral 10 designates blood port cover constituting part of housing 3. Blood port cover 10 is cap-like in shape and has end wall portion 10a facing circular end surface 1a of hollow fiber bundle 1 and peripheral wall portion 10b screwed on mount cover 6. By this screwing, end wall portion 10a is held in close contact with partitioning wall 2 via packing 11 provided on an edge portion of wall 2, thus defining a liquid tight blood port zone 12 in blood port cover 10. The inner surface of end wall portion 10a has annular grooved surface 13 having an arcuate sectional profile, and extending along and spaced apart from the edge of end surface 1a of hollow fiber bundle 1 and opposing surface 14 facing end surface 1a of hollow fiber bundle 1 and extending parallel to and at a small distance from end surface 1a. Thus, increased distance space 12a is defined between grooved surface 13 and edge portion of end surface 1a of hollow fiber bundle 1, and small distance space 12b is defined between opposed surface 14 and end surface 1a. Spaces 12a and 12b constitute blood port zone 12. Increased distance space 12a of blood port zone 12 communicates with blood port 15 extending in the radial direction of circular end surface 1a, as shown in FIGS. 4 and 5.

Figure 3:
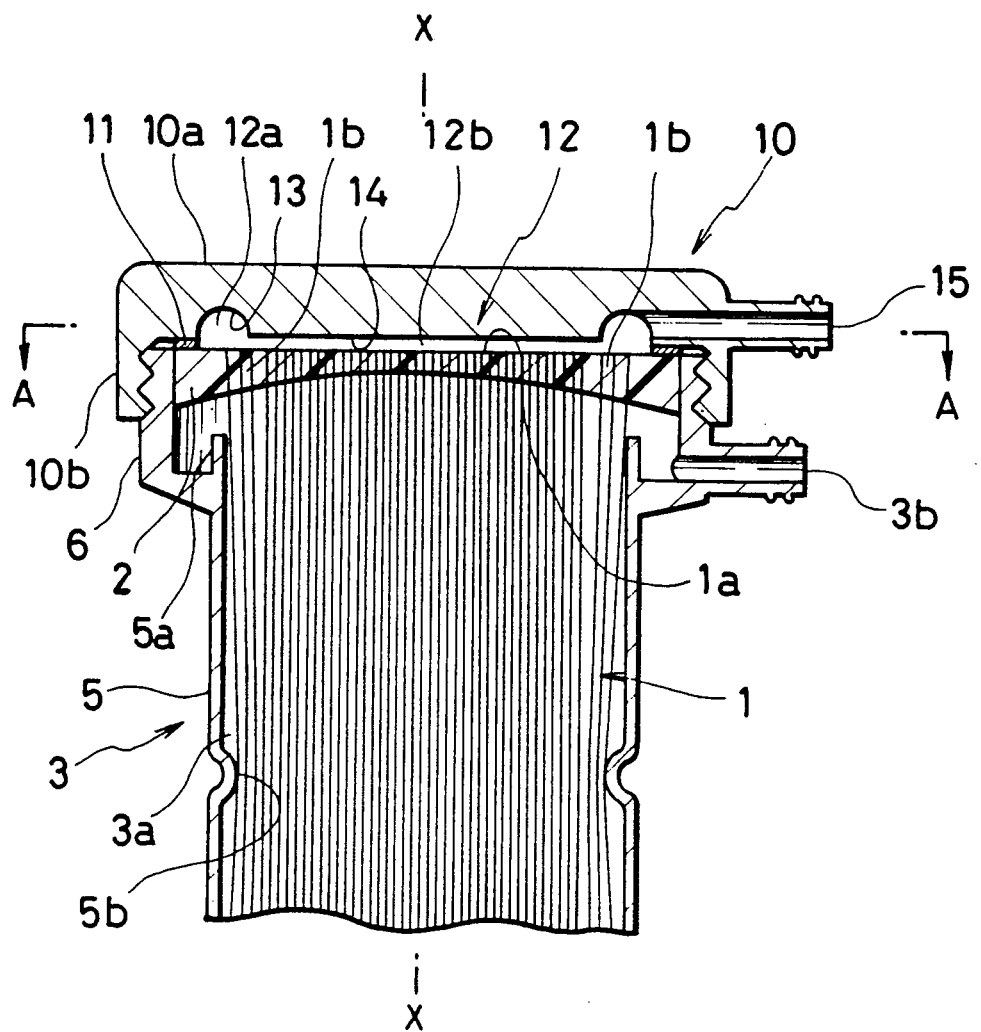
FIG. 3 is a fragmentary sectional view showing an oxygenator as a first embodiment of the blood processing circuit according to the invention.

With this oxygenator, in which small distance space 12b is formed uniformly and as a narrow space over the entire zone while increased distance space 12a is formed as a annular space, small distance space 12b offers high resistance against the flow of blood, while increased distance space 12a offers low resistance against the flow, and these two spaces are distinctly defined with respect to each other. Thus, where blood port zone 12 shown in FIG. 3 is the outlet side blood port zone, i.e., where blood having been subjected to gas exchange flows out through blood port 15, as shown in FIG. 4, blood emerging from the individual hollow fibers of hollow fiber bundle 1 flows through small distance space 12b uniformly and substantially in radial directions as shown by arrows to enter increased distance space 12a. In increased distance space 12a, blood flows more vigorously with reduced resistance offered against it. Thus, it is possible to secure sufficient blood flow on the side diametrically opposite blood port 15. Blood flows out from blood port 15 through increased distance space 12a as shown by arrows. Thus, blood flow along the periphery 1b of hollow fiber bundle 1 is increased to obtain uniform flow over the entire blood port zone 12. It is thus possible to prevent stagnation of blood and hence production of thrombus or clogging of hollow fibers.

Where blood port zone 12 shown in FIG. 3 is an inlet side blood port zone, blood entering increased distance space 12a from blood port 15 is first split into two streams flowing in opposite directions along increased distance space 12a. Then it flows uniformly and substantially in radial directions from increased distance space 12a into small distance space 12b as shown by arrows before entering the hollow fibers of hollow fiber bundle 1. Thus, it is possible to secure sufficient blood flow along the periphery 1b of the hollow fiber bundle and prevent stagnation.

The distance between opposed surface 14 and end surface 1a of hollow fiber bundle 1 in small distance space 12b is suitably between 1/20 and 1/300 of the diameter of hollow fiber bundle 1, preferably less than 1/30. If it is smaller than 1/20 of the diameter, more uniform blood flow can be obtained in radial directions as shown in FIGS. 4 and 5, and blood stagnation will never be produced in blood port zone 12 on the side thereof diametrically opposite blood port 15. If the distance is greater than 1/300 of the diameter, sufficient resistance against blood flow can be obtained in small distance space 12b, and nevertheless there is no possibility of rupture of blood cells due to high resistance against blood flow. Further, if increased distance space 12a has a width such that it radially extends beyond periphery 1b of hollow fiber bundle 1, the flow along the periphery 1b of hollow fiber bundle 1 can be increased.

However, to obtain sufficient blood flow along periphery 1b of hollow fiber bundle 1 the width of increased distance space 12a should not be extremely large; typically, it is suitably such that increased distance space 12a does not reach a circle concentric with and having one half the diameter of hollow fiber bundle 1.

Now, an oxygenator as a second embodiment of the invention will be described with reference to FIGS. 7 and 8. Referring to the Figures, reference numeral 20 designates a blood port cover, which is part of housing 3. It has end wall portion 20a as its main portion facing circular end surface 1a of hollow fiber bundle 1. The inner surface of end wall portion 20a has annular groove surface 23 formed along periphery 1b of hollow fiber bundle 1, annular end surface 26 formed as an end of annular rib 26a formed radially inwardly of grooved surface 23 and extending parallel to and at a small distance from end surface 1a of hollow fiber bundle 1 and central surface 27 formed radially inwardly of annular rib 26a. Thus, annular increased distance space 22a is defined between grooved surface 23 and the edge portion of end surface of hollow fiber bundle 1, annular small distance space 22b is formed between end surface 26 and an end surface of hollow fiber bundle 1, and central increased distance space 22c is formed between central surface 27 and an end surface of hollow fiber bundle 1. Spaces 22a to 22c constitute blood port zone 22. Annular increased distance space 22a of blood port zone 22, as shown in FIG. 8, communicates with blood port 25 extending in the radial direction.

Annular rib 26a is notched by notch 22d formed on the side of axis X—X diametrically opposite blood port 25, and thus annular increased distance space 22a communicates with small distance space 22b without the aid of central space 22c.

Figure 7:
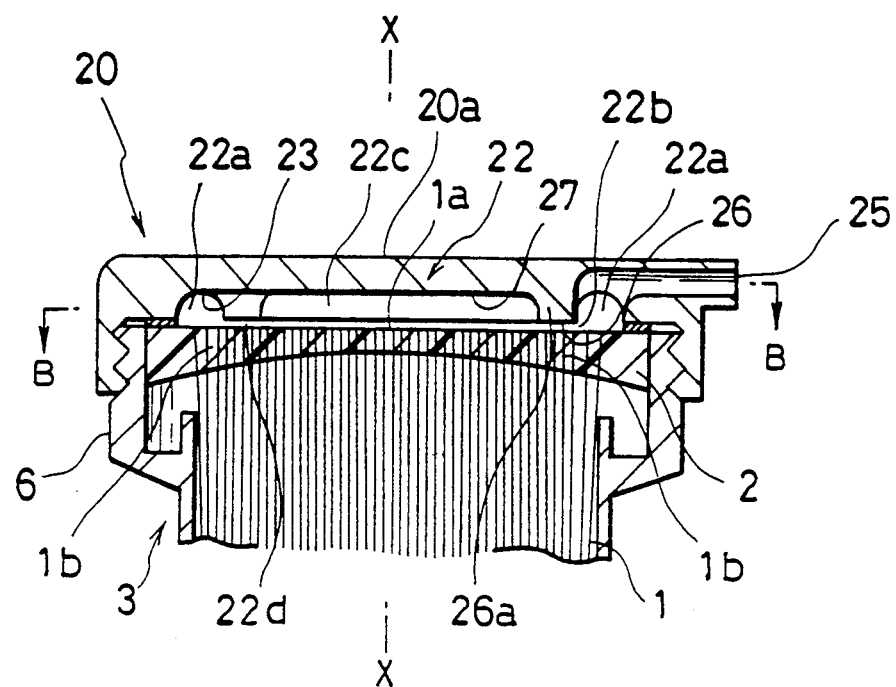
FIG. 7 is a fragmentary sectional view showing an oxygenator as a second embodiment of the blood processing apparatus according to the invention.
Figure 8:
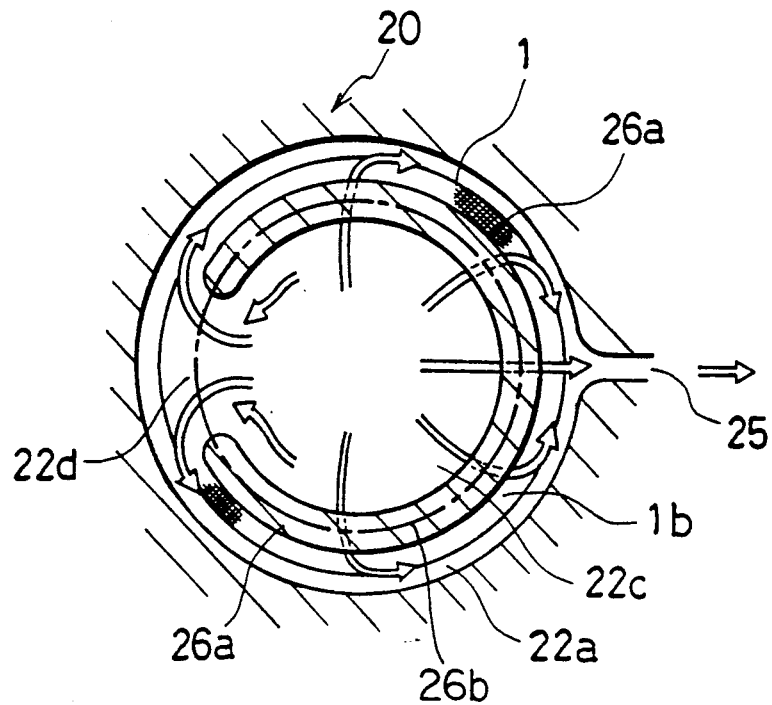
FIG. 8 is a fragmentary sectional view taken along line B—B in FIG. 7 for explaining the status of blood flow.

For the remainder of the structure, the second embodiment is the same as the previous first embodiment.

Where the oxygenator of the above construction is used such that blood port zone 22 is on the blood outlet side, blood flows greatly toward notch 22d of annular rib 26a, as shown by arrows in FIG. 8. More blood flows in opposite directions along increased distance space 22a, i.e., along periphery 1b of hollow fiber bundle 1, and blood stagnation is liable to be produced in this space portion. In this embodiment, blood flow is increased in an edge portion diametrically opposite blood port 25, so that it is possible to prevent blood stagnation, and hence production of thrombus or clogging of hollow fibers, over the entire blood port zone inclusive of the space portion noted above.

Where blood port zone 22 as shown in FIG. 7 is on the blood inlet side, although not shown, like the case described above in connection with the outlet side, blood smoothly flows through increased distance space 22 and forms a smooth blood flow from increased distance space 22a via notch 22d to central space 22c. Thus, satisfactory improvement of blood flow can be obtained particularly in a portion of the space diametrically opposite blood port 25 where stagnation of blood is liable to be produced.

Notch 22d formed in annular rib 26a satisfactorily has a length less than 2/5 of the circumference of a circle 26b passing through the center of the rib.

The distance between end surface 26 and end surface 1a of hollow fiber bundle 1 defining small distance space 22b is desirably less than 1/20 of the diameter of hollow fiber bundle 1. If the distance exceeds 1/20 of the diameter, the flow of blood to the periphery of hollow fiber bundle 1 is increased, while blood flow to a space portion diametrically opposite blood port 25 where stagnation is liable to occur is relatively reduced. Therefore, the effect of stagnation prevention is less effective.

Central surface 27 is desirably inclined toward notch 22d. In this case, the flow of blood toward notch 22d is promoted. The height of central increased diameter space 22c is desirably less than the height of annular increased diameter space 22a in view of obtaining smooth flow of blood from central increased distance space 22c to notch 22d.

Now an oxygenator as a third embodiment of the invention will be described with reference to FIG. 9. Referring to the Figure, reference numeral 30 designates a cylindrical peripheral wall member constituting part of housing 3. Peripheral wall member 30 is screwed on mount cover 6 and axially projects from the periphery of partitioning wall 2. By its screwing on mount cover 6, it is held in close contact via packing 31 with the edge portion of partitioning wall 2. Reference numeral 32 designates a circular movable member provided on the inner side of peripheral wall member 30 such that it faces open end surface 1a of hollow fiber bundle 1. Member 32 is axially movable toward and away from end surface 1a as shown by arrows in parallel therewith. Its surface facing end surface 1a of hollow fiber bundle 1 is parallel to end surface 1 in its edge portion 32a and has a spherical projection projecting toward end surface 1a in its central portion. It co-operates with end surface 1a to serve as movable wall means for varying the volume of the blood port zone. Its edge portion 32a is held in slidable close contact via packing 33 with the inner periphery of peripheral wall member 32, and blood port zone 34 is formed on its inner side. Blood port zone 34 is communicated with blood port 35 extending radially with respect to axis X—X of hollow fiber bundle 1.

For the remainder of the structure, this embodiment is the same as the previous first embodiment.

Figure 9:
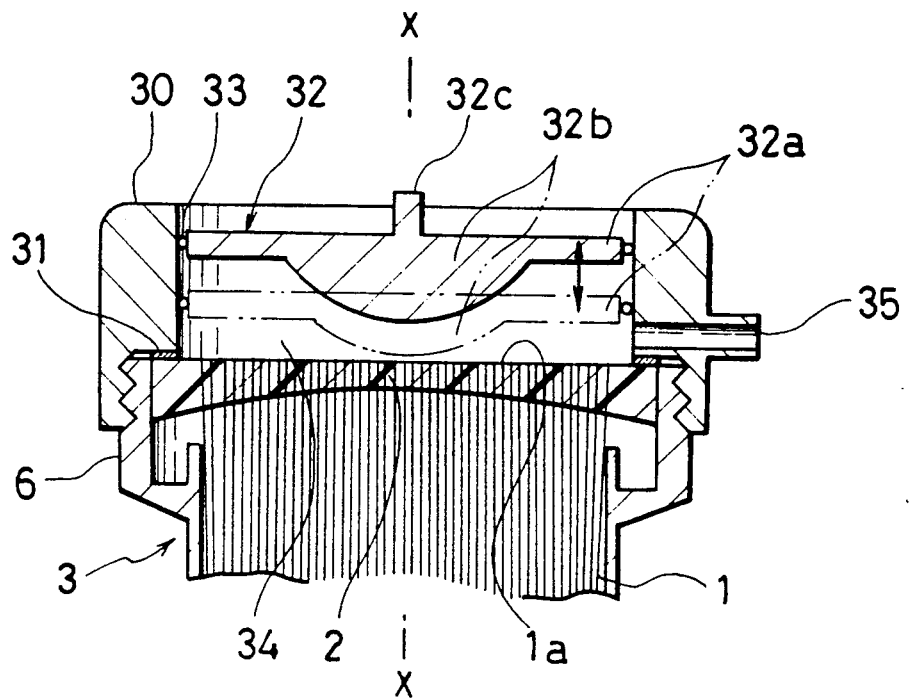
FIG. 9 is a fragmentary sectional view showing an oxygenator as a third embodiment of the blood processing apparatus according to the invention.

With the oxygenator of this construction, movable member 32 as movable wall means can be moved by an external driver (not shown) back and forth in vertical directions via operating end 32c, that is, it is movable toward and away from end surface 1a of hollow fiber bundle 1 between a position shown by solid line and a position shown by phantom line as shown by arrows in FIG. 9. By repeatedly reciprocally moving movable member 32 at a predetermined interval, a turbulent flow is produced in the blood flow positively with variations of the volume of blood port zone 34. Thus, it is possible to obtain smooth and positive flow of blood in the entire blood port zone and thus prevent stagnation of blood, and hence production of thrombus or clogging of hollow fibers.

Further, since movable member 32 has a spherically projecting central portion 32b other than edge portion 32a, blood port zone 34 is on the blood inlet side, sufficiently increased blood flow can be obtained even in periphery 1g of hollow fiber bundle 1 where stagnation of blood is particularly liable, and also a central space of the zone where stagnation is liable due to revolving flow is reduced. It is thus possible to prevent stagnation of blood more effectively.

Now, an oxygenator as a fourth embodiment of the invention will be described with reference to FIG. 10. Referring to the Figure, reference numeral 40 designates a cap member constituting part of housing 3. Cap member 40 has end wall portion 40a facing hollow fiber bundle 1 and cylindrical peripheral wall portion 40b. Peripheral wall portion 40b is screwed on mount cover 6, and by this screwing cap member 40 is held in close contact via the packing 41 with edge portion of partitioning wall 2. Reference numeral 42 designates a flexible membrane provided inside cap member 40 and capable of being elastically deformed. Member 42 serves as movable wall means and fulfills the same function as movable member 32 in the preceding third embodiment. It vertically divides the space in cap member 40 into two divisions, that is, it defines blood port zone 43 between it and end surface 1a of hollow fiber bundle 1 and pressure chamber 44 between it and end wall portion 40a. It is desirably made of silicone rubber, for instance.

Cap member 40 is provided with operating fluid port 46 communicating with pressure chamber 44 for introducing air or like operating fluid into chamber 44, that is, pressurized operating air can be supplied externally to pressure chamber 44 through port 46. Blood port zone 43 communicates with blood port 45 extending in the radial direction of end surface 1a like blood port 35 in the third embodiment.

For the remainder of the structure, this embodiment is the same as the first embodiment.

Figure 10:
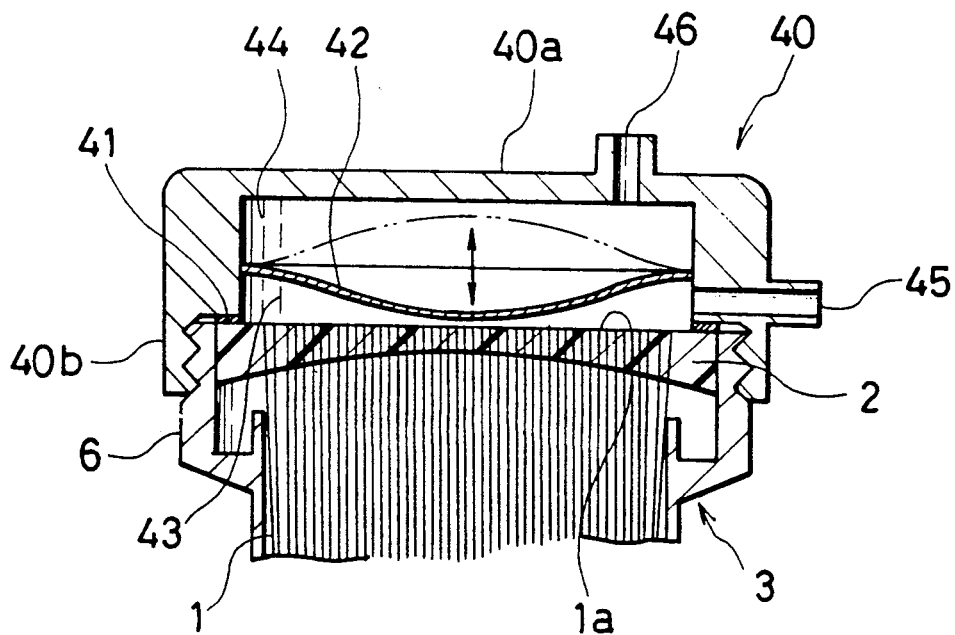
FIG. 10 is a fragmentary sectional view showing an oxygenator as a fourth embodiment of the blood processing apparatus according to the invention.

With the oxygenator of this structure, membrane 42 is reciprocally moved by elastic deformation like a diaphragm from the state shown by solid line to the state shown by phantom line as shown by arrows in FIG. 10 as the pressure in pressure chamber 44 is increased and reduced with pressurized air or like operating fluid introduced into and removed from chamber 44. In this way, stagnation of blood can be prevented.

Figure 11:
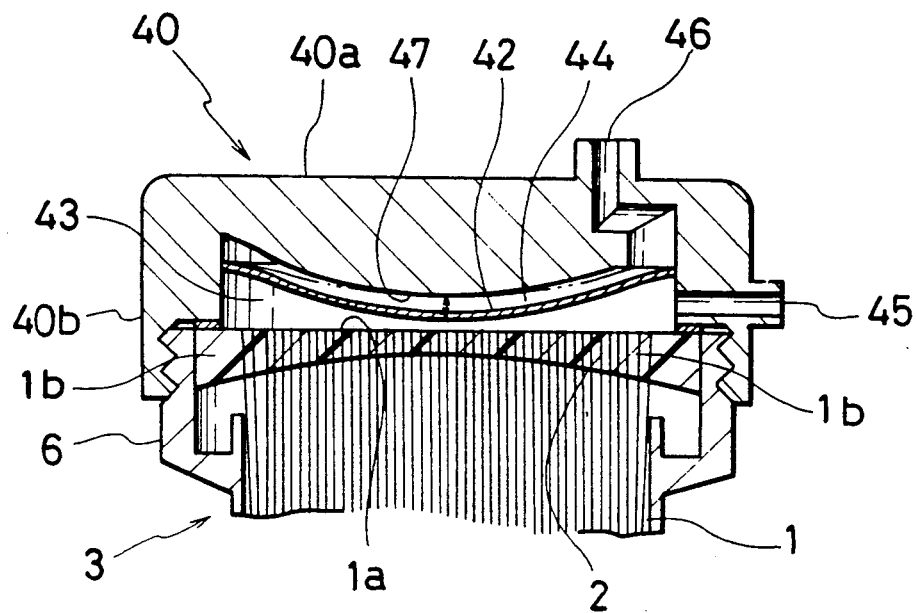
FIG. 11 is a fragmentary sectional view showing a modification of the fourth embodiment.

A modification of the fourth embodiment will now be described with reference to FIG. 11. Parts like those in the fourth embodiment are designated by like reference numerals.

In this instance, end wall portion 40a has spherically convex inner surface 47 projecting toward end surface 1a of hollow fiber bundle 1, and it serves as means for restricting the operation of membrane 42. That is, the deformation of membrane 42 is restricted due to contact thereof with inner surface 47. Membrane 42 thus can be held such that its central portion is closer to end surface 1a of hollow fiber bundle 1 than its edge portion. Thus, where blood port zone 43 is used for the blood inlet side with the deformation of membrane 42 restricted in the above way, blood port zone 43 can be held in a desired shape at all times to secure sufficient blood flow in peripheral portion 1b of hollow fiber bundle 1 and reduce central space of the zone where stagnation is liable to be caused by revolving flow, thus permitting further effective prevention of stagnation of blood.

In the above modification, the end wall portion 40a is formed integrally with the cap member 40 constituting part of housing 3. Alternatively the end wall portion 40a may be formed by a separate member different from the cap member 40 so as to have a spherical shape projecting toward the end surface 1a of the fiber bundle 1.

Now, an oxygenator as a fifth embodiment of the invention will be described with reference to FIG. 12. This embodiment, like the fourth embodiment, uses a membrane, and parts like those in the fourth embodiment are designated by like reference numerals. Blood port 45 is provided on the center of end wall portion of cap member 40 and extends axially. Membrane 42 is stretched in a curved fashion between the inner end of blood port 45 and the outer side of the edge of hollow fiber bundle 1 such that it flares toward the bundle. It defines blood port zone 43 between it and end surface 1a of hollow fiber bundle 1 and pressure chamber 44 between it and end wall portion 40a. Operating pressure of air or like operating fluid can be externally introduced into pressure chamber 44 through operating fluid port 46. Operating pressure in pressure chamber 44 causes reciprocal movement by deformation of membrane 42 between the state shown by solid line and the state shown by phantom line as shown by arrows in the Figure, thus varying the volume of blood port zone 43. In this way, turbulence can be positively produced in the blood flow in blood port zone 43 to provide for satisfactory flow of blood in an edge portion of zone 43 where stagnation is liable to be produced, providing for uniform flow of blood and preventing stagnation thereof.

In the foregoing, the first to fifth embodiments and a modification have been described. While these embodiments and modification of the blood processing apparatus of hollow fiber type according to the invention concerns an oxygenator, the invention is also applicable to other medical apparatuses such as artificial kidneys and further to industrial fields other than the medical apparatus field.

To confirm the effectiveness of the oxygenators of the above embodiments, the inventor conducted the following experiments.

EXPERIMENT 2

Figure 1:
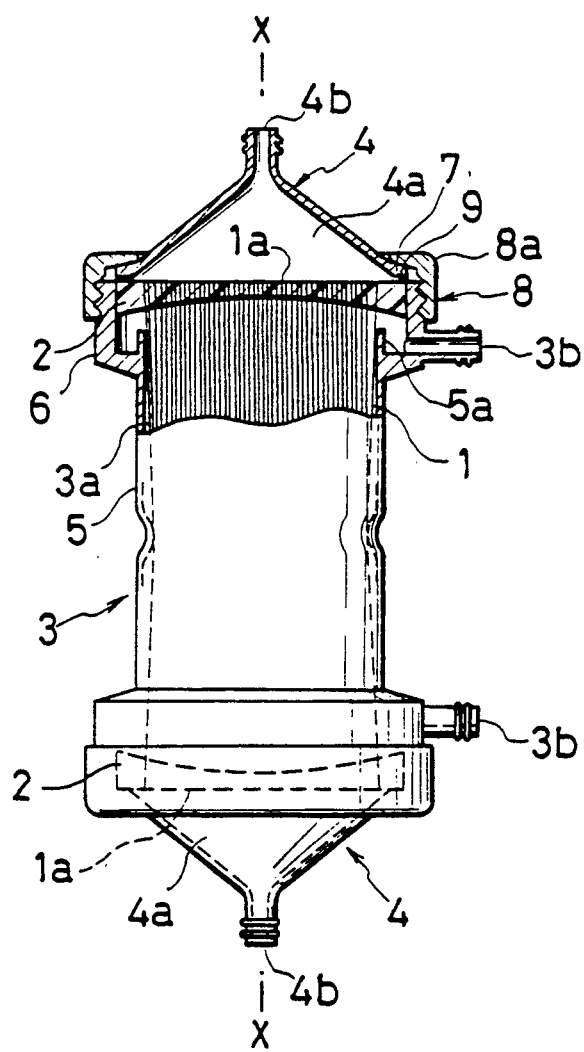
FIG. 1 is a front view, partly broken away, showing a prior art blood processing apparatus of hollow fiber type.
Figure 2:
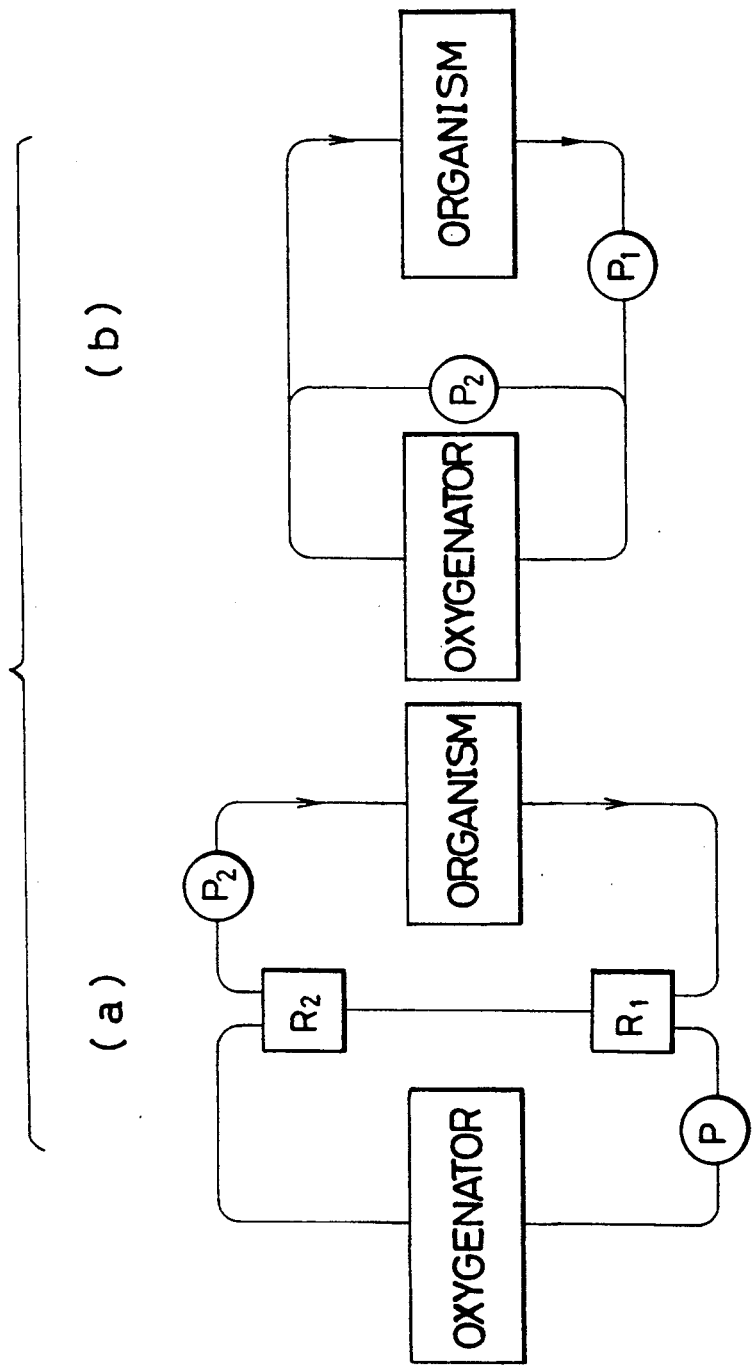
FIG. 2(a) is a circuit diagram showing an extracorporeal circulation circuit of a prior art blood processing apparatus with a re-circulation circuit with reservoirs.
FIG. 2(b) is a circuit diagram showing an extracorporeal circulation circuit of a prior art blood processing apparatus with a re-circulation circuit without any reservoir.

As the oxygenator according to the invention is used one, which is based on "Capiox Model II08" (a trade name of Terumo Co., Ltd.) having the same structure as shown in FIG. 1 and with a hollow fiber bundle diameter of 48 mm, and one of its blood port covers 4 is replaced with blood port cover 10 according to the first embodiment of the invention shown in FIG. 3. Modified type 1A was produced by setting the inner diameter of blood port cover 10 (i.e., outer diameter of increased distance space 12a) to 54 mm, the width of space 12a to 3 mm, height of space 12a to 3 mm, and height of small distance space 12b to 0.6 mm.

Modified type 1C was produced in the same way as modified type 1A except that the width of increased distance space 12a is set to 20 mm.

"Capiox II08" was used as Contrast 1D without any modification.

Figure 6:
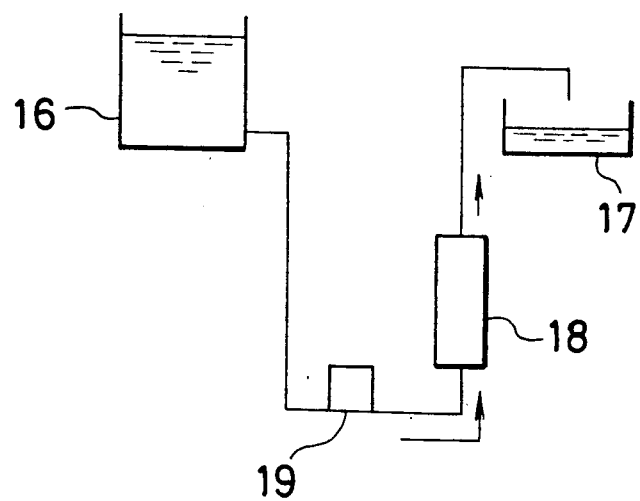
FIG. 6 is a circuit diagram for explaining a method of an experiment.

Modifications 1A to 1C and Contrast 1D were primed with water, and then 1-% toluidine blue (pigment) was charged into the blood port zones at the upper and lower ends of hollow fiber bundle 1. Then, each oxygenator 10 was piped to water supply tank 16 and water receiving tank 17 in vertical orientation such that substitute blood port cover 10 is on the upper side in an experiment circuit as shown in FIG. 6. Water was supplied as upward flow as shown by the arrow to oxygenator 18 from centrifugal pump 19 provided between water supply tank 16 and the oxygenator. The rate of flow of water was set to 200 ml/min. In this setting, residual pigment in the blood port zones was observed.

With the construction according to the invention, the degree of retention of the pigment, i.e., degree of washout, in outlet side blood port zone 10a was most satisfactory with Modified type 1B and then with Modified types 1A and 1C. Contrast 1D was inferior to any modified type according to the invention. With Modified types 1A and 1C slight retention of pigment was observed on the side opposite blood port 15. With Contrast 1D, retention of pigment was observed for a long time along the entire edge of hollow fiber bundle 1.

Modified type 1E and Contrast 1F were obtained from Modified type 1B and Contrast 1D, respectively, with covalent coupling of heparin to the materials of the hollow fibers and members defining the blood port zones.

The covalent coupling of heparin was obtained as follows. First, acryl polymer having a composition as shown in Table 1 was coated on the hollow fibers and other members. For the adjustment of polymer solution, one containing 15% of methyl selsolve was diluted with methanol or solution containing methanol and acetone in a ratio of 9:1 to obtain a 2.5-% polymer solution. Epoxy groups were introduced into a segment containing hydroxyethylmethacrylate (HEMA) by coupling glycidyl methacrylate (GMA), while acrylic acid (AA) was introduced into a segment containing methylmethacrylate (MMA).

TABLE 1

| HEMA segment HEMA/GMA (wt %) | MMA segment MMA/AA (wt %) |
|---|---|
| 68/12 | 17/3 |

Subsequently, amino groups were introduced into the coated surface of the hollow fibers and other members by reacting polyethyleneglycol diamine. Then heparin partly introduced primary amino groups were ion coupled, and then Schiff's base formed by treatment with gultaldehyde was reduced.

Modified type 1E and Contrast 1F thus obtained were used for non-heparin extracorporeal circulation using dogs for 10 hours and with the blood zones were observed for the formation of thrombus and clogging of hollow fibers.

With Contrast 1F, thrombus was observed along edge 1b of hollow fiber bundle 1. With Modified type 1E, thrombus was slightly observed in a very limited portion of a zone on the outer side of the edge of the hollow fiber blood port, but it was not observed in the rest of the zone at all. As for the clogging of hollow fibers, with Contrast 1F annular clogging was observed in edge portion 1b of hollow fiber bundle 1. With Modified type 1F, only very slight clogging was observed in edge portion 1b of hollow fiber bundle 1. With Modified type 1E, only very slight clogging was observed in an edge portion of the hollow fiber bundle opposite blood port 15.

EXPERIMENT 2

As the oxygenator according to the invention was used one, which was based on "Capiox II08" like Modified types 1A to 1C noted before, and one of blood port covers 4 of which was replaced with blood port cover 20 in the second embodiment as shown in FIG. 7. Modified type 2A was produced by setting the inner diameter of blood port cover 20 to 54 mm, width of increased distance space 22a to 6 mm, height of space 22a to 4 mm, lateral width of small distance space 22b to 9 mm, height of central increased distance space 22c to 3 mm and height of small distance space 22b to 0.4 mm and forming notch 22d over one-eighth of the circumference of annular rib 26a.

Modified type 2B was produced in the same way as Modified type 2A except that the height of central increased distance space 22c was set to 0.9 mm.

Contrast 2C was produced from Modified type 1B in Experiment 1 by setting the height of increased distance space 12a to 4 mm and height of small distance space 12b to 0.4 mm.

"Capiox II08" ws used as Contrast 2D without any modification.

With Modified types 2A and 2B and Contrasts 2C and 2D the degree of retention of pigment was observed in the same way as described before in connection with Experiment 1.

Wash-out was most satisfactory with Modified type 2B, then with Modified type 2A and Contrast 2C, and was considerably inferior with Contrast 2D. With Modified type 2A pigment vanished immediately. With Modified type 2A vanishment of pigment on the inner side of annular rib 26a was inferior to that with Modified type 2B. For space in notch 22d, a similarly satisfactory result to that with Modified type 2B could be obtained. With Contrast 2C, vanishment of pigment on the side opposite blood port 25 was inferior to those with Modified types 2A and 2B. With Contrast 2D pigment was retained for a long time along the edge of hollow fiber bundle 1.

Modified types 2E and 2F and Contrasts 2G and 2H were obtained from Modified types 2A and 2B and Contrasts 2C and 2D, respectively, with covalent coupling of heparin to the materials of the hollow fibers and members constituting the blood port zones.

The method of covalent coupling of heparin to the hollow fibers and other members was the same as in Experiment 1.

More specifically, with Modified types 2E and 2F and Contrasts 2G and 2H, an experiment of non-heparin extracorporeal circulation was conducted using dogs for observing the formation of thrombus and clogging of hollow fibers in the blood port zones. With Modified type 2F throumbus or clogging of hollow fibers in blood port zone was hardly recognized. With Modified type 2E only slight thrombus was recognized in an edge portion of central surface 27 on the inner side of annular rib 26a in blood port zone. With Contrast 2G thrombus and clogging of hollow fibers were observed very slightly on the side opposite blood port 25. With Contrast 2H thrombus was observed along the edge of hollow fiber bundle 1, and hollow fibers in this portion were found to be clogged.

EXPERIMENT 3

As the oxygenator according to the invention, Modified type 3A was produced from "Capiox II08" like Modified types 1A to 1C noted before by replacing one of blood port covers 4 with peripheral wall member 30 in the third embodiment shown in FIG. 9. Also, Modified type 3B was produced by replacing blood port cover 4 with cap member 40 in the fourth embodiment shown in FIG. 4. Further Modified types 3C and 3D were produced by using cap member 40 in the modification of the fourth embodiment shown in FIG. 11 and cap member 40 in the fifth embodiment shown in FIG. 12, respectively. As membrane 42 was used a silicone rubber membrane with a thickness of 200 microns.

Figure 13:
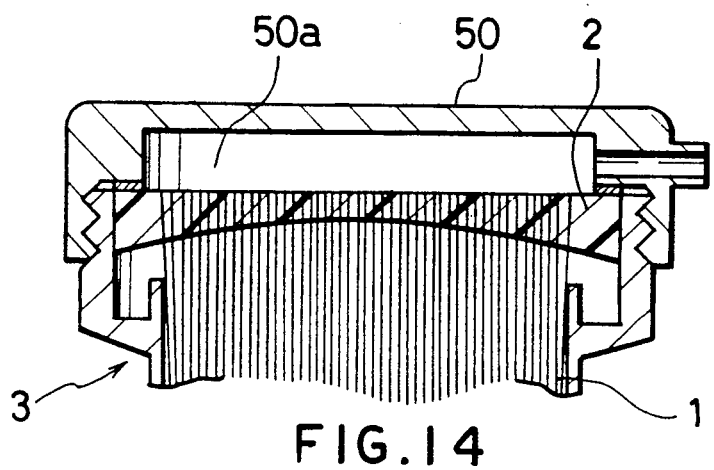
FIGS. 13 and 14 are fragmentary sectional views showing contrasts compared to the blood processing apparatus according to the invention.
Figure 14:
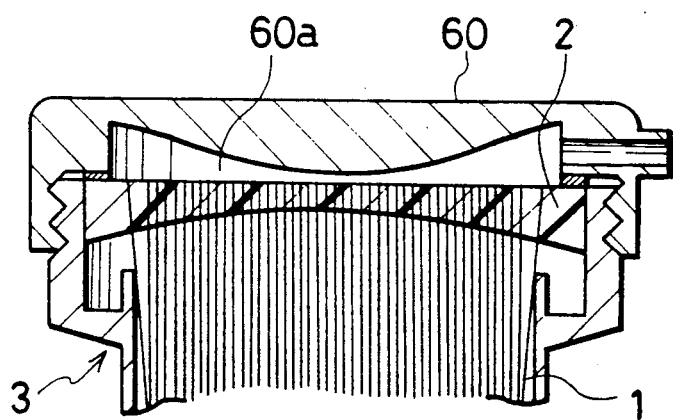

Further, Contrast 3E was produced by replacing blood port cover 4 with blood port cover 50 as shown in FIG. 13, defining blood port zone 50a just like a blood port zone defined when membrane 42 shown in FIG. 10 is parallel to the end surface of hollow fiber bundle 1. Further, Contrast 3F was produced by replacing blood port cover 4 with blood port cover 60 as shown in FIG. 14, defining blood port zone 60a having the same shape as blood port zone that is defined when membrane 42 shown in FIG. 11 is closest to end surface 1a of hollow fiber bundle 1. Further, "Capiox II08" was used as Contrast 3G without modification. For blood port covers 50 and 60 of Contrasts 3E and 3F polyurethane and acrylic resin were used.

With Modified types 3A to 3D and Contrats 3E to 3G, retention of pigment was observed in the manner as described before in connection with Experiment 1 by setting these apparatuses such that peripheral wall member 30, cap member 40 and blood port covers 50 and 60 were on the lower side, i.e., blood inlet side, and injecting pigment into the inlet side blood port zone.

Figure 15:
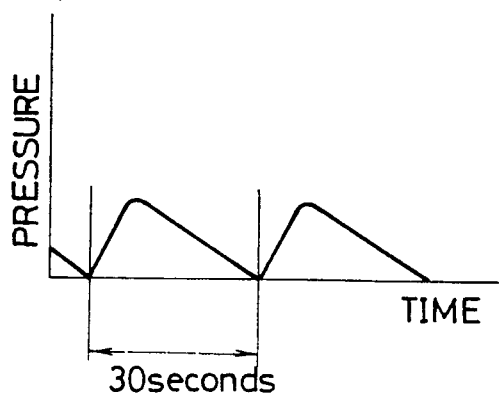
FIG. 15 is a graph illustrating an interval of air supply to a pressure chamber.

With modified types 3B to 3D, when repeatedly supplying operating air pressure to pressure chamber 44 at an interval of 30 seconds as shown in FIG. 15 for reducing pressure in pressure chamber 44, the rate of suction of air or like operating fluid is held within the rate of blood flow (i.e., 200 ml/min. as in Experiment 1). If the suction rate exceeds this value, the increase of the volume of blood port zone 43 due to pressure reduction in pressure chamber 44 exceeds the quantity of blood entering zone 43 to set a negative pressure in zone 43. Besides, since the hollow fibers were porous, in blood processing chamber 3a blood in the hollow fibers and ambient air are in direct contact with each other, so that it is possible that ambient air is sucked into hollow fibers. Where the hollow fibers are made of a diffusive membrane, blood is never in direct contact with air, and hence the above hazardousness can be avoided.

Wash-out was equally satisfactory with Modified types 3A, 3C and 3D, then with Modified type 3B, and was considerably inferior with Contrasts 3E and 3F in the mentioned order. The retention of pigment in the blood port zone one minute after injection of pigment was as follows. Modified types 3A, 3C and 3D were transparent, while Modified type 3B was colored very slightly. With Contrast 3E pigment remained in the central space, and with Contrast 3F it also remained, but to a lesser extent, in the central space. With contrast 3G, it was recognized along the edge.

Further, Modified type 3D was set in the experimental flow circuit such that cap member 40 is on the upper blood outlet side, and for comparison to Contrast 3G pigment was injected into the outlet side blood port zone, and retention of pigment in the outlet side blood port zone was observed.

With Contrast 3G pigment remained in the edge portion even after one minute from the injection of pigment, but with Modified type 3D no pigment was recognized.

Figure 12:
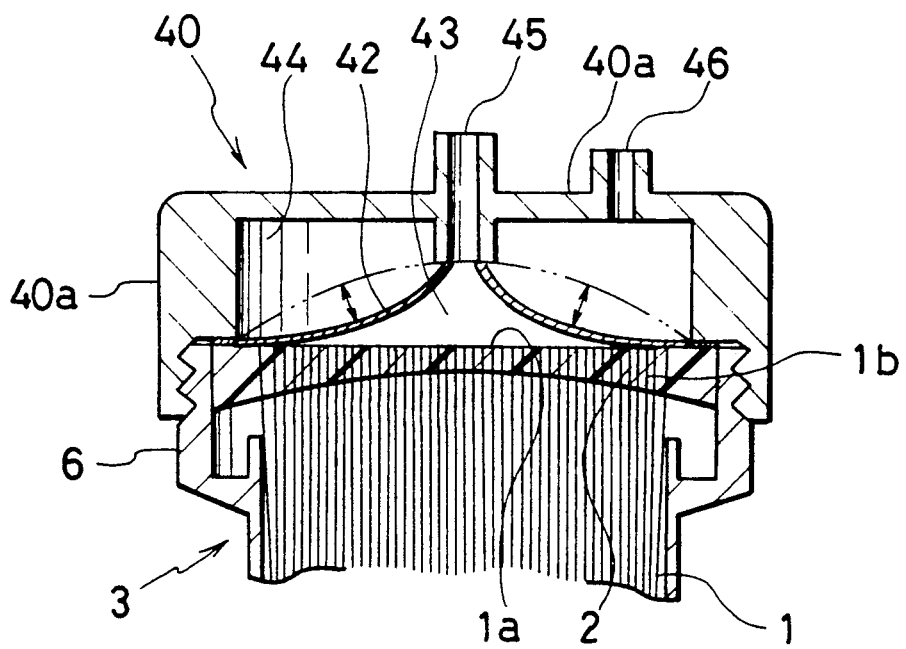
FIG. 12 is a fragmentary sectional view showing an oxygenator as a fifth embodiment of the blood processing apparatus according to the invention.

Further, Modified type 3H was produced from "Capiox II08" by replacing both upper and lower blood port covers 4 with cap members 40 shown in FIG. 12 and using hollow fibers with covalently coupled heparin. Further, Contrast 3I was produced from "Capiox II08" by commonly coupling heparin to the hollow fibers. Heparin was commonly coupled in the same way as in Experiment 1.

With Modified type 3H and Contrast 3I an experiment of non-heparin extracorporeal circulation was conduced using dogs in the manner as in Experiment 1.

With Contrast 3I the oxygenator was closed in 6 hours, whereas with Modified type 3H the apparatus was hardly closed even after 10 hours.

As has been shown, with the above embodiments and modifications thereof of the the blood processing apparatus of hollow fiber type according to the invention, with the formation of the annular increased distance space provided along an edge portion of the hollow fiber bundle and small distance space defined inside the annular increased instance space, in the blood port zone, and/or with the provision of the movable member in the blood port zone for varying the volume thereof, it is possible to secure sufficient and uniform blood flow and proclude blood stagnation in the entire blood port zone including spaces adjacent to edge and central portions of the hollow fiber bundle, thus preventing the formation of thrombus and clogging of hollow fibers.

Figure 16A:
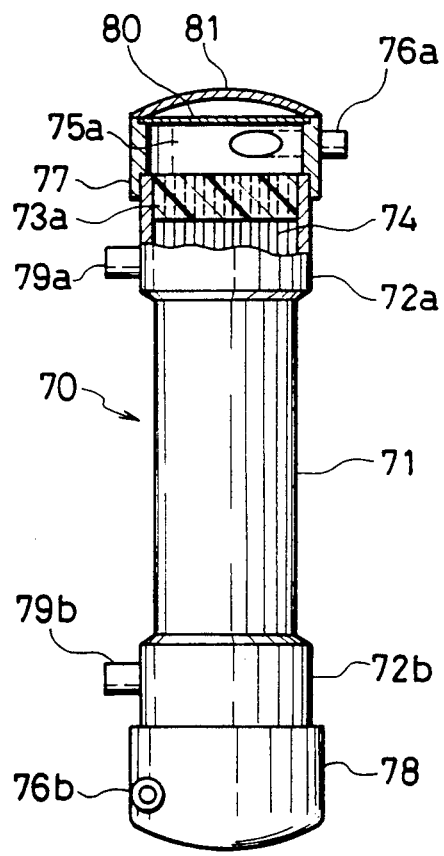
FIG. 16(a) is a front view, partly broken away, showing an oxygenator as a sixth embodiment of the blood processing apparatus according to the invention.
Figure 16B:
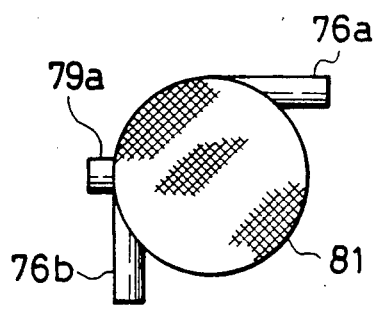
FIG. 16(b) is a plan view showing the same embodiment of the oxygenator.

Now, a sixth embodiment of the invention will be described with reference to FIGS. 16(a) and 16(b).

This embodiment again is oxygenator 70 comprising cylindrical body 71 with opposite end portions 72a and 72b. Hollow fiber bundle 74 comprising a large number of hollow fibers is secured at each end to partitioning wall 73a secured to the inside of each of end portions 72a and 72b such that it is open to blood port zone 75a. The periphery of blood port zone 75a is defined by peripheral wall member 76a secured to an end of end portion 72a. Blood inlet pipe 77 comprising one blood ductline is connected to peripheral wall member 77. Reference numeral 80 designates a flexible rubber membrane having a thickness of 100 microns. Membrane 80 can be readily deformed according to variations of pressure of blood in blood port zone 75a. Thus, when a pressure variation in blood port zone 75a is produced by blood flowing into zone 75a from inlet pipe 76a, flexible membrane 80 is deformed according to the pressure variation, thus maintaining stable pressure in blood port zone 75a at all times. The edge of flexible membrane 80 has its edge secured by bonding to the open end of peripheral wall member 77, thus defining a liquid tight blood port zone 75a. Over flexible membrane 80, i.e., outside blood port zone 75a, net-like member 81 of a metal or a plastic material, constituting restricting means for restricting the deformation of membrane 80, is secured to the open end of peripheral wall member 77 so as to clamp flexible membrane 80 between it and member 77. As shown in FIG. 6(a), net-like member 81 is spherically curved to be convex with respect to flexible membrane 80. Thus, when flexible membrane 80 is deformed according to a blood pressure variation, particularly when blood port zone 75a is increased in volume due to excessive pressure, its excessive deformation can be restricted. Further, since netlike member 81 is spherical in shape, flexible membrane 80, which otherwise could be deformed excessively, is brought to uniform contact with the entire inner surface of member 81. Thus, a restricting force is applied to flexible membrane 80 uniformly to avoid damage to membrane 80.

As the other end hollow fiber bundle 74, like the above blood port zone, blood port zone 78 is formed, which is defined by peripheral wall member 72b and has a blood inlet port. Blood inlet pipe 76b as the other blood ductline is communicated with this blood port zone. Inlet and outlet ports 79a and 79b are provided for oxygen or like blood purifying medium.

Figure 17A:
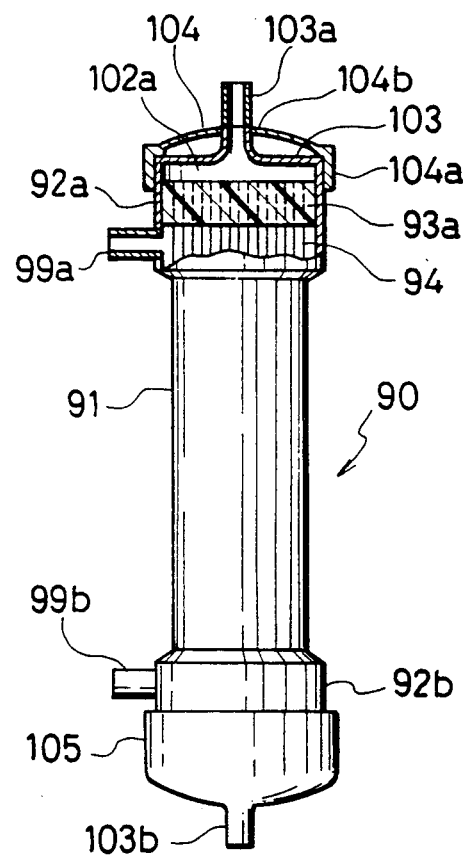
FIG. 17(a) is a fragmentary sectional view showing an oxygenator as a seventh embodiment of the blood processing apparatus according to the invention.
Figure 17B:
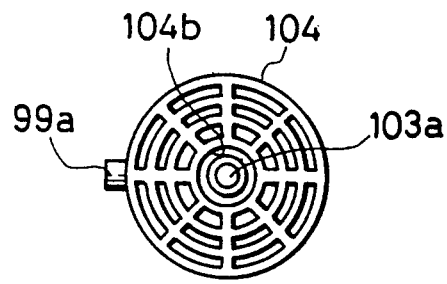
FIG. 17(b) is a plan view showing the seventh embodiment of the oxygenator.

FIGS. 17(a) and 17(b) designate a seventh embodiment. In this embodiment of oxygenator 90, like the preceding sixth embodiment, hollow fiber bundle 94 comprising of a large number of hollow fibers is secured at one end to partitioning wall 93a secured to the inside of end portion 92a of cylindrical body 91 such that it is open to blood port zone 102a. The periphery of blood port zone 102a is defined by peripheral wall member 92a. Reference numeral 103 designates a flexible silicone rubber membrane with a thickness of 100 microns and having integral central blood inlet pipe 103a serving as one blood ductline. When pressure variations are produced in blood port zone 102a, membrane 103 is deformed according to the pressure variation to maintain stable pressure in blood port zone 102a at all times.

The edge of flexible membrane 103a is secured by bonding to the open end of peripheral wall member 92a, thus defining a liquid tight blood port zone 102a. Over flexible membrane 103, i.e., outside blood port zone 102a, restricting means for restricting the deformation of membrane 103 is provided. The restricting means is constituted by net-like member 104 of polycarbonate. Member 104 has rim-like portion 104a which is fittedly secured to the outer periphery of an end portion of peripheral wall member 92a such that flexible membrane 103 is clamped between rim portion 104a and peripheral wall member 92a. Net-like member 104 has central hole 104b, through which blood pipe 103 extends. Net-like member 104, as shown in FIG. 17(a), is spherically curved such that it is convex with respect to the flexible membrane. Thus, when flexible membrane 103 is deformed according to pressure variations of blood entering blood port zone 102a, its excessive deformation can be restricted particularly when blood port zone 102a is increased in volume due to excessive pressure increase.

At the other end of the hollow fiber bundle, like blood port zone 105 is defined by peripheral wall member 92b and has a blood inlet port secured thereto. Blood inlet pipe 103b as the other blood ductline is connected to the blood port and communicates with the blood port zone.

Figure 19:
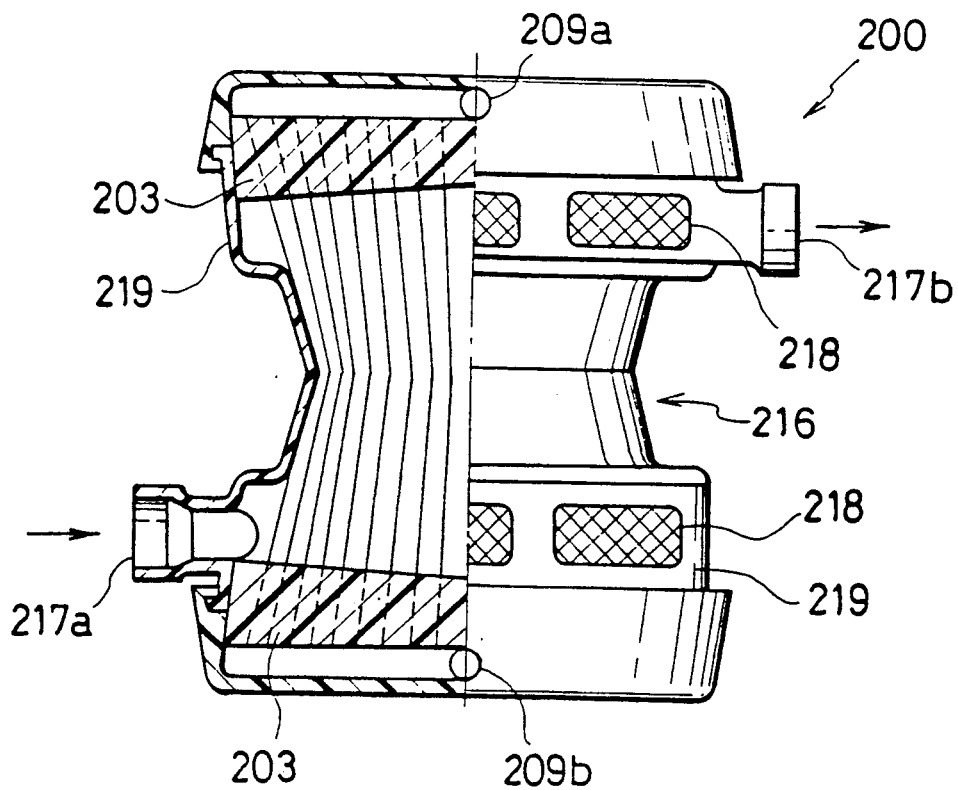
FIG. 19 is a front view, partly broken away, showing an oxygenator as an eighth embodiment of the blood processing apparatus according to the invention.

FIG. 19 shows an eighth embodiment of the invention. This embodiment is different from the preceding sixth and seventh embodiments in the location of the flexible membrane. More specifically, this embodiment of oxygenator 200 is an oxygenator of extracorporeal circulation type, in which blood is caused to flow on the outer side of the hollow fiber bundle and oxygen gas on the inner side. Blood introduced from blood inlet pipe 217a passes through a space defined between the hollow fiber bundle and cylindrical body 216 to be led out through blood outlet pipe 217b. Cylindrical body 216 has opposite end increased diameter portions 219 which are provided with flexible membranes 218 for buffering pressure variations due to variations of blood flow. Again in this embodiment, a spherically curved net-like member like in the sixth and seventh embodiments may be provided in position corresponding to each flexible membrane 218 as restricting means for restricting the deformation of membrane 218.

EXPERIMENT 4

Figure 18:
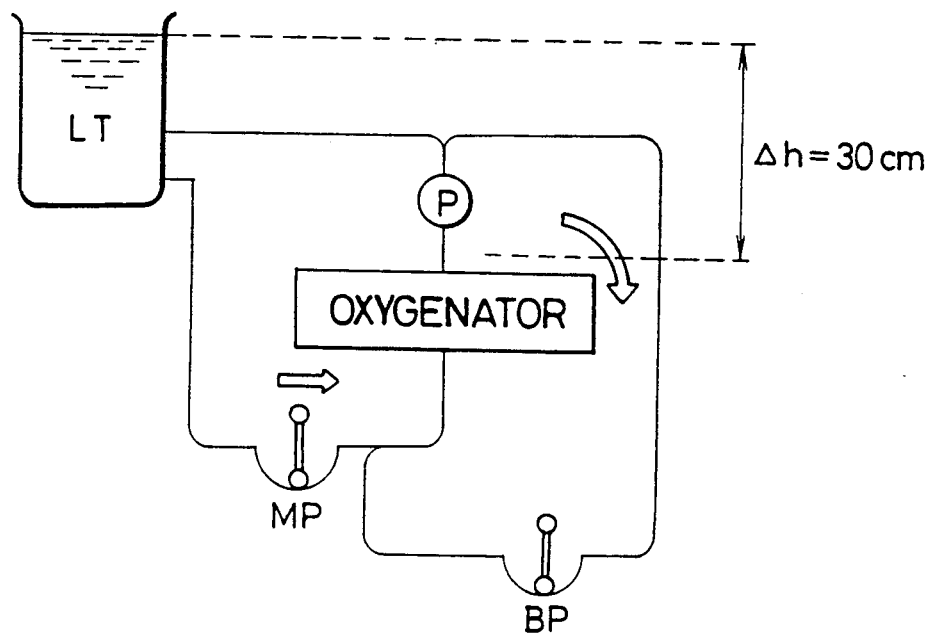
FIG. 18 is a circuit diagram showing a circuit used for tests.

For comparing the performance of the sixth to eighth embodiments of oxygenators (with membrane area of 3.3 m$^2$), characteristics of these oxygenators were measured using a flow circuit shown in FIG. 18. Contrast No. 4 was used for the sixth and seventh embodiments, and Contrasts No. 5 and No. 6 for the eighth embodiment.

Referring to FIG. 18, designated at LT is a liquid tank, MP and BP are main and bypass pumps, respectively, and P a pressure sensor. As the pumps, roller pumps were used. The oxygenators of the embodiments and contrasts were installed at the illustrated position of oxygenator in the circuit for measurement. With each oxygenator the minimum flow from bypass pump BP, with which bubbles from the oxygenator can be observed with the eyes, in each flow from main pump MP was measured.

In each measurement, liquid tank LT was filled with an aqueous solution with the viscosity thereof adjusted to 3 centipoises with glycerine, and the minimum flow (1/min.) from bypass pump BP, with which bubbles are generated from the oxygenator, was measured with the flow from main pump MP set to 500, 600 and 700 ml/min. Table 2 shows the results. In Table 2, A represents the sixth embodiment, B the seventh embodiment, C Contrast No. 4, D the eighth embodiment, and E Contrast No. 5.

As is obvious from Table 2, with either embodiment A or B of the oxygenator according to the invention, no bubbles were generated even with the permissible maximum flow in the oxygenator. In contrast, with the prior art oxygenator, bubbles were generated with a comparatively low flow rate. It was thus recognized that according to the invention, unlike the prior art, bubbles are difficultly generated even when the oxygenator is set in the a circuit having two pumps (i.e., pumps MP and BP).

In each test, pressure at point P was measured, and the minimum flow from BP, at which momentary negative pressure was generated, was measured. The results of measurements are shown in Table 3.

From this result, it was confirmed that with the embodiments according to the invention it is possible to prevent generation of negative pressure.

TABLE 2

| Flow from MP (ml/min) | Minimum flow from BP, with which bubbles are generated (l/min) | | | | |
|---|---|---|---|---|---|
| | A | B | C | D | E |
| 500 | 3.5< | 3.5< | 2.0 | 5.5< | 1.5 |
| 600 | 3.4< | 3.4< | 2.5 | 5.4< | 2.0 |
| 700 | 3.3< | 3.3< | 3.0 | 5.3< | 2.0 |

*The minimum clinical flow with the oxygenator according to the invention was 4 l/min. and no greater flow was studied for A and B. Likewise, no greater flow was studied for D, the maximum flow of which was 6.0 l/min.

TABLE 3

| Flow from MP (ml/min) | Minimum flow from BP when momentary negative pressure is generated (l/min) | | | | |
|---|---|---|---|---|---|
| | A | B | C | D | E |
| 0 | 4< | 4< | 0.3 | 6.0< | 0.3 |
| 150 | 3.85< | 3.85< | 0.6 | 5.85< | 0.6 |
| 300 | 3.7< | 3.7< | 0.6 | 5.7< | 0.6 |
| 600 | 3.4< | 3.4< | 0.6 | 5.4< | 0.6 |

While flexible membranes 80 and 103 in above embodiments are provided in both the inlet and outlet side blood port zones, it is possible to provide a membrane only in the outlet side blood port zone in order to prevent momentary negative pressure for preventing introduction of bubbles. To prevent momentary pressure increase and negative pressure, it is desirable to provide a membrane for each of the inlet and outlet blood ports. Further, various other changes and modifications of the above embodiments are possible without departing from the scope of the invention.

As has been described in the foregoing, with the above sixth to eighth embodiments of the blood processing apparatus according to the invention, at least part of the blood flow path is constituted by a flexible membrane deformable according to blood pressure variations. Thus, it is possible to absorb pressure variations. In addition, there is no hazardousness of rupture of blood cells due to generation of negative pressure in the blood flow path. Further, there is no possibility of introduction of bubbles into the hollow fiber bundle.

Thus, the blood processing apparatus according to the invention permits ready re-circulation of blood without any storage unit, thus permitting an efficient blood processing.

Further, by providing a restricting member in correspondence to the flexible membrane for preventing excessive deformation of the flexible membrane, it is possible to obtain a safer and more durable blood processing apparatus.

What is claimed is:

1. A blood processing apparatus of the hollow fiber type, comprising:
   a hollow fiber bundle having a plurality of open ended hollow fibers through which blood flows, wherein the open ends of the hollow fibers form circular open end surfaces at opposite ends of said hollow fiber bundle;
   a housing accommodating said hollow fiber bundle and including at each end thereof an end wall surface extending substantially parallel to and spaced from a respective circular open end surface of said hollow fiber bundle;
   each end wall surface including:
   an annular groove formed along a periphery thereof and spaced a first distance from said respective circular open end surface of said hollow fiber bundle;
   an annular rib integrally projecting toward said respective circular open end surface of said hollow fiber bundle and spaced therefrom a second distance, wherein said annular rib is positioned radially inwardly with respect to a respective annular groove of said respective end wall surface;
   and a central surface formed radially inwardly of a respective annular rib and spaced a third distance from said respective circular open end surface of said hollow fiber bundle;
   wherein said second distance is less than said first distance and said third distance, and said third distance is no greater than said first distance;
   each said end wall surface defining a blood port zone between said housing and said respective circular open end surface of said hollow fiber bundle;
   said housing including means defining a blood port at each end thereof in fluid flow communication with a respective blood port zone, each of said blood ports extending in a radial direction with respect to said respective circular open end surface of said hollow fiber bundle;
   wherein each said annular rib includes a notch formed on a side of a central longitudinal axis of said hollow fiber bundle diametrically opposite a respective blood port;
   whereby reach radially extending blood port and respective blood port zone are constructed and arranged to promote uniform flow of blood over an entire said respective end surface of said hollow fiber bundle, thus positively preventing stagnation of blood in said respective blood port zone.

2. The blood processing apparatus according to claim 1, wherein:
   said hollow fiber bundle has a given diameter, and
   said second distance is 1/20 to 1/300 of the diameter of said hollow fiber bundle.

3. The blood processing apparatus according to claim 2, wherein said second distance is 1/30 to 1/300 of the diameter of said hollow fiber bundle.

4. The blood processing apparatus according to claim 1, wherein said notch has a length which is no greater than 2/5 of a length of a circle passing through a center of said rib.

5. A blood processing apparatus of the hollow fiber type, comprising:
- a hollow fiber bundle having a plurality of open ended hollow fibers through which blood flows, wherein the open ends of the hollow fibers form open end surfaces at opposite ends of said hollow fiber bundle;
- a housing accommodating said hollow fiber bundle, said housing having opposite end portions;
- means defining a blood port at each end portion of said housing;
- means defining a blood port zone inside said housing at each end portion of said housing, each blood port zone being in fluid flow communication with a respective blood port;
- an elastically deformable flexible membrane in at least one of said blood port zones for varying a volume of said at least one of said blood port zones; said elastically deformable flexible membrane facing a respective open end surface of said hollow fiber bundle with a respective blood port zone interposed therebetween; said elastically deformable flexible membrane being supported by said housing to be substantially parallel to said respective open end surface of said hollow fiber bundle and movable in a longitudinal axial direction of said hollow fiber bundle toward and away from said respective open end surface of said hollow fiber bundle;
- at least one pressure chamber formed in said housing and arranged on a side of a respective at least one flexible membrane which faces a respective end portion of said housing, for applying pressure to said flexible membrane; and
- at least one operating fluid inlet means provided on said housing for externally introducing operating fluid into a respective at least one pressure chamber to thereby apply pressure to said flexible membrane.

6. A blood processing apparatus according to claim 5, wherein:
- said hollow fiber bundle has a given diameter,
- said open end surfaces of said hollow fiber bundle are substantially circular, said at least one flexible membrane has a substantially circular shape corresponding to said circular open end surfaces of said hollow fiber bundle and having a central portion which is constructed and arranged to project into said respective blood port zone toward said respective open end surface of said hollow fiber bundle, and
- each of said blood ports extending in a radial direction with respect to said circular open end surfaces of said hollow fiber bundle.

7. The blood processing apparatus according to claim 5, which further comprises:
- restricting means on said housing for restricting deformation of said at least one flexible membrane.

8. A blood processing apparatus of the hollow fiber type, comprising:
- a hollow fiber bundle having a plurality of open ended hollow fibers;
- a housing accommodating said hollow fiber bundle, said housing having opposite end portions;
- means defining a blood port at each end portion of said housing;
- means defining a blood port zone inside said housing at each end portion of said housing, each blood port zone being in fluid flow communication with a respective blood port;
- an elastically deformable flexible membrane in at least one of said blood port zones for varying a volume of said at least one of said blood port zones provided in said housing and spaced from a respective end of said hollow fiber bundle;
- at least one restricting means on said housing arranged adjacent said at least one flexible membrane for restricting deformation of said flexible membrane;
- at least one pressure chamber formed in said housing arranged on a side of said at least one flexible membrane which faces a respective end portion of said housing, for applying pressure to said flexible membrane; and
- at least one operating fluid inlet means provided on said housing for externally introducing operating fluid into a respective at least one pressure chamber to thereby apply pressure to said flexible membrane.

9. A blood processing apparatus of the hollow fiber type, comprising:
- a hollow fiber bundle having a plurality of open ended hollow fibers;
- a housing accommodating said hollow fiber bundle, said housing having opposite end portions;
- means defining a blood port at each end portion of said housing;
- means defining a blood port zone inside said housing at each end portion of said housing, each blood port zone being in fluid flow communication with a respective blood port;
- an elastically deformable flexible membrane in at least one of said blood port zones for varying a volume of said at least one of said blood port zones provided in said housing and spaced from a respective end of said hollow fiber bundle;
- at least one restricting means on said housing arranged adjacent said at least one flexible membrane for restricting deformation of said flexible membrane; and
- wherein said at least one restricting means has a substantially spherical shape and projects toward said respective end of said hollow fiber bundle from a respective end portion of said housing.

10. The blood processing apparatus according to claim 9, wherein said at least one restricting means comprises an inner wall surface at an end portion of said housing.

11. A blood processing apparatus of the hollow fiber type, comprising:
- a hollow fiber bundle having a plurality of open ended hollow fibers;
- a housing accommodating said hollow fiber bundle, said housing having opposite end portions;
- means defining a blood port at each end portion of said housing;
- means defining a blood port zone inside said housing at each end portion of said housing, each blood port zone being in fluid flow communication with a respective blood port;
- an elastically deformable flexible membrane in at least one of said blood port zones for varying a volume of said at least one of said blood port zones provided in said housing and spaced from a respective end of said hollow fiber bundle;

at least one restricting means on said housing arranged adjacent said at least one flexible membrane for restricting deformation of said flexible membrane; and wherein said at least one restricting means comprises a net member provided in a respective end portion of said housing on a side of said flexible member which faces said respective end portion, said net member projecting substantially spherically outwardly toward said flexible membrane from said housing.

* * * * *

UNITED STATES PATENT AND TRADEMARK OFFICE
CERTIFICATE OF CORRECTION

PATENT NO. : 5,139,741
DATED : August 18, 1992
INVENTOR(S) : HAGIWARA, Kazuhiko

It is certified that error appears in the above-identified patent and that said Letters Patent is hereby corrected as shown below:

Column 9, line 63, change the phrase "with edge"
    to read --with the edge--.

Column 11, line 20, change "EXPERIMENT 2" to read
    --EXPERIMENT 1--.

Column 18, line 51 (claim 1), change the phrase
    "whereby reach" to read --whereby each--.

Title page, Abstract, line 10, delete the letters "V" in
    both the instances.

Signed and Sealed this

Twenty-third Day of November, 1993

Attest:

BRUCE LEHMAN

Attesting Officer

Commissioner of Patents and Trademarks